United States Patent [19]

Walker et al.

[11] Patent Number: 5,128,324
[45] Date of Patent: Jul. 7, 1992

[54] TRANSDERMALLY APPLICABLE PHARMACEUTICAL PREPARATIONS WITH STEROLINES AND/OR SPIROKETALINES

[75] Inventors: Hans Walker, Eschwege, Fed. Rep. of Germany; Karl H. Pegel, Durban Natal, South Africa

[73] Assignee: Roecar Holdings, Willemstad, Netherlands

[21] Appl. No.: 399,581

[22] Filed: Aug. 28, 1989

[30] Foreign Application Priority Data

Sep. 1, 1988 [DE] Fed. Rep. of Germany ....... 3829641

[51] Int. Cl.⁵ .................... A61K 31/705; A61K 47/00
[52] U.S. Cl. ....................................... 514/26; 514/27; 514/947; 424/449
[58] Field of Search ................... 424/449; 514/947, 26, 514/27

[56] References Cited

U.S. PATENT DOCUMENTS

| | | |
|---|---|---|
| 3,966,918 | 6/1976 | Kawamata et al. ................. 424/182 |
| 4,188,379 | 2/1980 | Pegel ...................................... 514/26 |
| 4,254,111 | 3/1981 | Pegel et al. ........................... 514/26 |
| 4,260,603 | 4/1981 | Pegel et al. ........................... 514/26 |
| 4,265,886 | 5/1981 | Pegel ...................................... 514/26 |
| 4,461,762 | 7/1984 | Malinow ............................... 514/26 |
| 4,602,003 | 7/1986 | Malinow ............................... 514/26 |

FOREIGN PATENT DOCUMENTS 0162330 11/1985 European Pat. Off. .
2458890 6/1975 Fed. Rep. of Germany .
3401178 7/1985 Fed. Rep. of Germany ........ 514/26
3416112 10/1985 Fed. Rep. of Germany .
2039217 8/1980 United Kingdom .

OTHER PUBLICATIONS

Seki et al. "Plasma Lipoproteins as Drug Carriers: Pharmacological Activity and Disposition of the Complex of -Sitosteryl- -D-glucopyranoside with Plasma Lipoproteins". *Journal of Pharmaceutical Sciences*, vol. 74, No. 12 (Dec. 1985), pp. 1259–1264.

Seifen-Ole-Fette-Wachse, Band 109, No. 15, Sep. 1983, pp. 444–445, Verlag fur Chemische Industire, H. Ziolkowsky KG, Augsburg, DE C.-E. Loevberg: "Holzbasierendes beta-Sitosterin-ein Rohstoff fur die Kosmetikindustri e".

Seifen-Ole-Fette-Wasche, Band 112, No. 8, Mai 1986, pp. 261–262, Verlag fur Chemische Industrie, H. Ziolkowsky KG, Augsburg, DE; A. Hamunen et al.: "Sterine aus unverseifbaren Bestandteilen des Tallols–ein auf Holz basierendes Rohmaterial ur die Kosmetik-, Pharma- und Lebensmittelindustrie".

European Search Report.

Primary Examiner—Shep K. Rose

[57] ABSTRACT

The invention relates to novel, transdermally applicable pharmaceutical preparations including sterolines or spiroketalines, a solvent selected from the group consisting of ethoxylated sterols and C12–C30 alcohols, and lipophilic ointment base. Methods of treatment using same.

13 Claims, No Drawings

TRANSDERMALLY APPLICABLE PHARMACEUTICAL PREPARATIONS WITH STEROLINES AND/OR SPIROKETALINES

FIELD OF THE INVENTION

The invention relates to novel, transdermally applicable pharmaceutical preparations having a steroline and/or spiroketaline content.

BACKGROUND OF THE INVENTION

The glycosides of phytosterols, including cholesterol, are called sterolines. Phytosterols and their glycosides occur in nature in small amounts in all plants and often in microorganisms. It is possible to produce sterolines synthetically in relatively large yields by means of the known Königs-Knorr synthesis with the use of the corresponding aglycones and a sugar acetate bromided at the C-1 position with the use of silver or cadmium catalysts. In nature, sterolines mostly occur in the form of monoglycosides, although some oligoglycosides are known. Additionally, sterolines occur in natural vegetable matter, partially also in the form of esters, namely in monobasic monocarboxylic acids.

Mono- to triglycosides, derived from steroid saponine alcohols, which have a spiroketaline grouping connected in the C-16 and C-17 position of the steroid shell of aglycone, are called spiroketalines. The aglycones can be classified either as 5-En-steroid sapogenines or as 5-α-steroid sapogenines. In natural saponine material the aglycones are mainly present as glycosides and contain 3 or possibly more coupled monosaccharide units and can be hydrolytically decomposed to spiroketalines by means of enzymes. Synthesis of spiroketalines by the Königs-Knorr method is also possible with good yields. It has been known for a long time that both sterolines as well as spiroketalines exhibit a multitude of pharmacological activities because they interact at the prostaglandinesynthetase level, as known from British Patent 2 039 217, as well as at the lipoxygenase level, as known from German Published, Non-examined Application DE-OS 34 16 112, for example. Thus sterolines and spiroketalines can be used not only for the treatment of inflammatory conditions, but also wherever it is necessary to normalize the arachidonic acid balance, for example with asthma, acne, psoriasis, abdominal rheumatism, gastric and intestinal ulcers, and thrombophlebitis.

Up to now, in the use of sterolines in particular, it has been shown that excellent results in the course of in vitro testing could not be reproduced in vivo. In J. Pharm Sci., 1985, 74, pp 1259, J. Seki et al have noted an intestinal absorption of sitosterol glycoside of only 1 to 2%. This often occurs because the extremely poor water solubility of the sterolines and the poor water solubility of spiroketalines makes it impossible to achieve sufficient resorption and thus blood levels. For this reason there has been a previous attempt to improve resorption, for example by reducing the particle size, by using more highly water-soluble derivatives such as hemiesters, or by using solubilizers, such as recited, for example, in U.S. Pat. No. 3,966,918. Tests using substances marked with $^{14}C$, however, clearly show that resorption can only be slightly improved by use of a micronizer or other reduction of the particle size, and that this is also true when an attempt is made to increase the amount of the compounds in the aqueous solution by using solubilizers.

Thus there is still a need for pharmaceutical preparations containing sterolines and/or spiroketalines and having better resorptivity.

SUMMARY OF THE INVENTION

In accordance with the invention, pharmaceutical preparations which are administered transdermally are provided, which have a content of sterolines and/or spiroketalines with ethylene oxide addition compounds having approximately 20 to 30 ethylene oxide units of sterols or alcohols.

In a completely surprising way, it is possible to dissolve the sterolines and spiroketalines, which are hard to dissolve not only in water, but as a rule also in lipophilic solvents, in an oil phase with the id of solubilizers and even if they are in the form of emulsions, to bring them to resorption transdermally, and this at a far higher resorption than has ever been possible orally or intravascularly.

In accordance with the invention, the active ingredients are mixed together with ethoxylated sterols or C12-C30 alcohols, which had been reacted with ethylene oxide, and were dissolved in multivalent alcohols, such as 1,2-propanediol or glycerine, with slight heating. All ethoxylated sterols or C12-C30 alcohols can be used as solubilizers and carriers, either in mixture or as mono compounds. These compounds which can be easily manufactured by reacting the free alcohols with ethylene oxide, are partially already known as solubilizers and commercially available as for example the products sold by Henkel KGaA under the name "Generol-E". They are mostly sitosterol or sterol mixtures with a degree of ethoxylatation between 20 to 30. Preferably an ethoxylated sitosterol with a chain length of 25 EO units is used. It is possible to use fatty alcohols, in particular, as alcohols with approximately 12 to 30 C atoms, but of course also naturally occurring branched, alicyclic or aromatic alcohols such as squalene or phytol derivates, for example, are usable.

The solutions of sterolines or spiroketalines in solubilizers and multivalent alcohols in turn dissolve clearly in oil or melted fat. The customary ointment bases are mainly used for this such as, for example, central chain triglycerides, glycerol monostearate, lanolin, lard, etc. It has also been shown in a completely surprising manner that it is possible, after working the active ingredients into the fatty bases, to continue by making the latter into emulsion ointments, because the mixture can be readily emulsified with an equal amount of water. Regardless of whether the active ingredients are present in a water-free or aqueous fat base, tests with $^{14}C$ marked active ingredients have shown that penetration into the skin and permeation follow at approximately the same amounts. Not only do the active ingredients penetrate the skin, they even permeate through the skin so that, with an application over a large area, it is possible to attain plasma levels to a degree not possible via the intestinal route. Surprisingly, in spite of the different chemical structure of sterolines and spiroketalines there is hardly any difference in respect to the transdermal resorption. As shown by the $^{14}C$ tests, twenty-four hours after application approximately 10% of the active ingredients have permeated through the skin and approximately 6% have penetrated into the skin.

The average composition for transdermal application is approximately 0.1% active ingredients, 1% ethylene oxide addition compounds and 10% multivalent alcohol. After dissolving, the clear solution is either mixed with a corresponding amount of waterless ointment base or, in a manner known per se, is mixed with approximately one half of the amount of ointment base with the addition of the customary amount of noniogenic emulsifying agents as well as water and is emulsified in the customary way with the remaining amount under stirring.

During clinical tests it has been possible to obtain particularly fast and persuasive results with the pharmaceutical preparations according to the invention in connection with those diseases, where an elevated leucotriene level is the basis or at least a mediator of the pathological event such as, for example, with allergies, eczemas, chronic itching, certain types of psoriasis, acne, but also with rheumatoid diseases and thrombophlebitis.

The invention is described in detail below by means of the examples.

DETAILED DESCRIPTION

Example 1

0.1 g cholesterol glycoside, 80.0 g ethoxylated palmytilstearyl alcohol were dissolved in 100.0 g 1,2-propanediol. This solution, heated to 70° C., was added to a melt of 120.0 g adeps solidus, 100.0 g of central chain triglyceride and 120 g glycerine monostearate at a temperature of 70° C. and was emulsified with water, also heated to the temperature indicated above, into a total amount of 1,000.0 g. Then the emulsion was stirred until cool.

Example 2

1.0 g diosgenin glycoside was dissolved in a mixture of 10.0 g ethoxylated soybean sterol (25 EO units) and 100.0 g 1,2-propanediol. This solution, heated to 70° C. was then added to a melt, also heated to 70° C., of 100.0 g cetyl palmitate, 250.0 g stearyl heptanoate, 100.0 g sorbitan monostearate and 60.0 g polyethylene sorbitan monostearate and was emulsfied with water, also heated to 70° C., to a total amount of 1,000.0 g. The emulsion was then stirred until cool in a manner known per se.

Example 3

1.0 g sitosterol glycoside was dissolved in 10.0 g ethoxylated soybean sterol (25 EO units) and 100.0 g 1,2-propanediol and was added at the temperatures indicated to a melt of 300.0 g hydrated coconut oil, 50.0 g central chain triglycerides, 120.0 g glycerine monostearate and 80.0 g ethoxylated cetyl stearyl alcohol (25 EO units). An emulsion was made with water heated to 70° C. to a total amount of 1,000.0 g. The emulsion was then stirred until cool as usual.

Example 4

1.0 g sitosterol glycoside was dissolved in 10.0 g ethoxylated soybean sterol (25 EO units) and 100.0 g 1,2-propanediol and was added at the temperatures indicated to a melt of 300.0 g hydrated coconut oil, 50.0 g central chain triglycerides, 20.0 g glycerine monostearate and 80.0 g ethoxylated cetyl stearyl alcohol (25 EO units). An emulsion was made with water heated to 70° C. to a total amount of 1,000.0 g. The emulsion was then stirred until cool as usual.

Example 5

Penetration or Permeation Measurements

Male rabbits, about 10 weeks old and weighing approximately 2 kg, were used as test animals. On a shaved area of $10 \times 5$ cm on the back of the rabbit 1.0 g ointment having a radioactivity of 20 $\mu$ Ci of the respective ($^{14}$C-4) marked glycoside was applied, covered with aluminum foil and fixed with a waterproof bandage. After 24 hours the rabbits were put to sleep and the application area was repeatedly washed with ethanol moistened swabs. The radioactivity of the occlusive dressing and the swabs was measured after extraction with ethanol. The skin of the application area was treated for 24 hours with 2 m lye/methanol/triton X 405 (6:3:1 v/v) at 55° C. and was then washed with ethanol at 40° C. The radioactivity, measured with a liquid scintillation counter (Philips PW 4700), is a measurement for the percentage of penetration of the applied amount of the substance. Permeation during 24 hours is calculated as follows: 100%—(activity of the washing liquid+activity of the penetration amount)=% permeation. Under the test condition cited, the result for cholesterol glycoside was a penetration of 4.9% of the applied dosage and a permeation of 7.8% of the applied dosage. The results for diosgenin glycoside were 5.2 and 10.3% and for sitosterol glycoside the results were 6.2 and 10.6%.

What is claimed is:

1. Transdermally applicable pharmaceutical preparations comprising:
   a transdermally effective amount of sterolines or spiroketalines;
   a solvent selected from the group consisting of ethoxylated sterols and ethoxylated C12-C30 alcohols; and
   lipophilic ointment base.

2. Pharmaceutical preparations in accordance with claim 1, wherein said sterols and C12-C30 alcohols have approximately 20 to 30 ethylene oxide units.

3. Pharmaceutical preparations in accordance with claim 1, wherein said sterol is sitosterol with approximately 25 EO units.

4. Pharmaceutical preparations in accordance with claim 1 wherein said lipophilic ointment is a water/oil emulsion.

5. Pharmaceutical preparations in accordance with claim 1 wherein said solvent is selected from the group consisting of branched alcohols, alicyclic alcohols and aromatic alcohols.

6. Pharmaceutical preparations in accordance with claim I wherein said solvent is a squalene or phytol derivate.

7. Pharmaceutical preparations in accordance with claim 1 wherein said sterolines or spiroketalines are present in an amount averaging 0.1% by weight, and said solvent is present in an amount averaging 10% by weight containing an average amount of 1% by weight ethylene oxide.

8. A method of treating conditions wherein an elevated leucotriene level is the basis or at least a mediator, which comprises applying to the skin a transdermally effective amount of a pharmaceutical preparation including sterolines or spiroketalines; a solvent selected from the group consisting of ethoxylated sterols and ethoxylated C12-C30 alcohols; and lipophilic ointment base.

9. The method of claim 8 wherein said sterolines or spiroketalines penetrate said skin in an amount ranging from 4.9-6.2% of the applied amount.

10. The method of claim 8 wherein said sterolines or spiroketalines permeate said skin in an amount ranging from 7.8-10.6% of the applied amount.

11. A method of treating rheumatoid conditions and thrombophlebitis which comprises applying to the skin a transdermally effective amount of a pharmaceutical preparation including sterolines or spiroketalines; a solvent selected from the group consisting of ethoxylated sterols and ethoxylated C12-C30 alcohols; and lipophilic ointment base.

12. The method of claim 11 wherein said sterolines or spiroketalines penetrate said skin in an amount ranging from 4.9-6.2% of the applied amount.

13. The method of claim 11 wherein said sterolines or spiroketalines permeate said skin in an amount ranging from 7.8-10.6% of the applied amount.

* * * * *